US00PP20089P2

(12) United States Plant Patent
Jandrew

(10) Patent No.: US PP20,089 P2
(45) Date of Patent: Jun. 9, 2009

(54) ***CUPHEA* PLANT NAMED 'RI REEDA'**

(50) Latin Name: *Cuphea procumbens*
Varietal Denomination: Ri Reeda

(75) Inventor: Jason Jandrew, Gilroy, CA (US)

(73) Assignee: Goldsmith Seeds Inc., Gilroy, CA (US)

( * ) Notice: Subject to any disclaimer, the term of this patent is extended or adjusted under 35 U.S.C. 154(b) by 0 days.

(21) Appl. No.: 12/150,466

(22) Filed: Apr. 28, 2008

(51) Int. Cl.
*A01H 5/00* (2006.01)

(52) U.S. Cl. ..... Plt./420
(58) Field of Classification Search ..... Plt./420
See application file for complete search history.

*Primary Examiner*—Annette H Para
(74) *Attorney, Agent, or Firm*—C. A. Whealy

(57) ABSTRACT

A new and distinct cultivar of *Cuphea* plant named 'Ri Reeda', characterized by its compact and low mounding growth habit; freely branching habit; freely flowering habit; large red-colored flowers that are held above the foliage on strong pedicels; and good garden performance.

2 Drawing Sheets

Botanical designation: *Cuphea procumbens.*
Cultivar denomination: 'Ri Reeda'.

BACKGROUND OF THE INVENTION

The present invention relates to a new and distinct cultivar of *Cuphea,* botanically known as *Cuphea procumbens* and hereinafter referred to by the name 'Ri Reeda'.

The new *Cuphea* is a product of a planned breeding program conducted by the Inventor in Gilroy, Calif. The objective of the breeding program is to create new compact and freely branching *Cuphea* cultivars with numerous and attractive flowers and good garden performance.

The new *Cuphea* originated from a cross-pollination made by the Inventor in July, 2002 in Gilroy, Calif. of a proprietary selection of *Cuphea procumbens* identified as code number 26-2, not patented, as the female, or seed, parent with a proprietary selection of *Cuphea procumbens* identified as code number 16-1, not patented, as the male, or pollen, parent. Seeds collected from the stated cross-pollination were sown in September, 2003. The new *Cuphea* was discovered and selected by the Inventor as a single flowering plant within the progeny of the stated cross-pollination in a controlled greenhouse environment in Gilroy, Calif. December, 2003.

Asexual reproduction of the new *Cuphea* by cuttings in a controlled greenhouse environment in Gilroy, since January, 2004, has shown that the unique features of this new *Cuphea* are stable and reproduced true to type in successive generations.

SUMMARY OF THE INVENTION

Plants of the new *Cuphea* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Ri Reeda'. These characteristics in combination distinguish 'Ri Reeda' as a new and distinct cultivar of *Cuphea:*

1. Compact and low mounding growth habit.
2. Freely branching habit.
3. Freely flowering habit.
4. Large red-colored flowers that are held above the foliage on strong pedicels.
5. Good garden performance.

Plants of the new *Cuphea* can be compared to plants of the parent selections. Plants of the new *Cuphea* differ from plants of the female parent selection in the following characteristics:

1. Plants of the new *Cuphea* have smaller leaves than plants of the female parent selection.
2. Plants of the new *Cuphea* have shorter internodes than plants of the female parent selection.
3. Plants of the new *Cuphea* have larger flowers than plants of the female parent selection.

Plants of the new *Cuphea* differ from plants of the male parent selection in the following characteristics:

1. Plants of the new *Cuphea* have smaller leaves than plants of the male parent selection.
2. Plants of the new *Cuphea* have larger flowers than plants of the male parent selection.
3. Plants of the new *Cuphea* and the male parent selection differ in flower color as plants of the male parent selection have magenta-colored flowers.

Plants of the new *Cuphea* can also be compared to plants of the *Cuphea* 'Firefly', not patented. In side-by-side comparisons conducted in Gilroy, Calif. plants of the new *Cuphea* differed from plants of 'Firefly' in the following characteristics:

1. Plants of the new *Cuphea* had shorter internodes than plants of 'Firefly'.
2. Plants of the new *Cuphea* had larger flowers than plants of 'Firefly'.
3. Plants of the new *Cuphea* had brighter red-colored flowers than plants of 'Firefly'.

BRIEF DESCRIPTION OF THE PHOTOGRAPHS

The accompanying colored photographs illustrate the overall appearance of the new *Cuphea,* showing the colors as true as it is reasonably possible to obtain in colored reproductions of this type. Colors in the photographs may differ slightly from the color values cited in the detailed botanical description which accurately describe the colors of the new *Cuphea*.

The photograph on the first sheet comprises a side perspective view of a typical flowering plant of 'Ri Reeda' grown in a container.

The photograph on the second sheet is a close-up view of typical flowers of 'Ri Reeda'.

DETAILED BOTANICAL DESCRIPTION

The aforementioned photographs and following observations, measurements and values describe plants grown in Gilroy, Calif. during the late summer in a polyethylene-covered greenhouse and under conditions which approximate commercial *Cuphea* production. During the production of the plants, day temperatures ranged from 24° C. to 32° C. and night temperatures averaged 18° C. Rooted young plants were pinched one time and had been growing for about four months when the photographs and description were taken. In the following description, color references are made to The Royal Horticultural Society Colour Chart, 2001 Edition, except where general terms of ordinary dictionary significance are used.

Botanical classification: *Cuphea procumbens* cultivar Ri Reeda.

Parentage:

*Female, or seed, parent.*—Proprietary selection of *Cuphea procumbens* identified as code number 26-2, not patented.

*Male, or pollen, parent.*—Proprietary selection of *Cuphea procumbens* identified as code number 16-1, not patented.

Propagation:

*Type.*—By cuttings.

*Time to initiate and develop roots.*—About seven to ten days.

*Root description.*—Fibrous, fleshy; white in color.

*Rooting habit.*—Freely branching.

Plant description:

*Plant and growth habit.*—Herbaceous annual. Compact and low mounding growth habit. Freely branching habit, about three to five lateral branches per plant; early pinching enhances branching.

*Plant height.*—About 12 cm to 13 cm.

*Plant diameter.*—About 24 cm to 26 cm.

Lateral branch description:

*Length.*—About 13 cm to 17 cm.

*Diameter.*—About 3 mm to 4 mm.

*Internode length.*—About 1.3 cm to 3.3 cm.

*Aspect.*—Mostly upright.

*Texture.*—Hirsute.

*Color.*—Close to 145B.

Foliage description:

*Arrangement.*—Opposite; simple.

*Length.*—About 4.5 cm to 4.7 cm.

*Width.*—About 2.3 cm to 2.7 cm.

*Shape.*—Ovate.

*Apex.*—Acute.

*Base.*—Obtuse.

*Margin.*—Entire.

*Texture, upper and lower surfaces.*—Hirsute; slightly rugose.

*Venation pattern.*—Pinnate.

*Color.*—Developing foliage, upper surface: Close to 137A. Developing foliage, lower surface: Between 138A and 138B. Fully developed foliage, upper surface: Slightly darker than 137A; venation, close to 145B. Fully developed foliage, lower surface: Between 138A and 138B; venation, close to 145B.

*Petiole length.*—About 3 mm to 4 mm.

*Petiole diameter.*—About 2 mm.

*Petiole texture, upper and lower surfaces.*—Hirsute.

*Petiole color, upper and lower surfaces.*—Close to 142B.

Flower description:

*Flower arrangement and habit.*—Single flared tubular flowers. Freely flowering habit with about five to seven flowers per cluster. Flowers persistent. Flowers face mostly outwardly.

*Fragrance.*—None detected.

*Natural flowering season.*—Plants flower continuously from the spring through the early fall in California.

*Flower longevity.*—Individual flowers last about one week on the plant.

*Flower diameter, horizontal axis.*—About 3.5 cm to 3.7 cm.

*Flower diameter, vertical axis.*—About 3 cm to 3.3 cm.

*Flower length.*—About 3.5 cm to 4 cm.

*Flower bud.*—Shape Tubular; slightly orbicular towards the apex. Length: About 1.3 cm to 1.6 cm. Diameter, towards the apex: About 6 mm to 8 mm. Color: Close to 53C.

*Corolla.*—Arrangement: Six petals arranged in a single whorl; two banner (dorsal) petals, two lateral petals and two lower petals. Banner petals: Length: About 1.9 cm to 2.2 cm. Width: About 1.9 cm to 2.2 cm. Shape: Spatulate. Apex: Emarginate or rounded. Base: Truncate. Margin: Entire; undulate. Texture, upper and lower surfaces: Hirsute; rugose. Color: When opening and fully opened, upper surface: Close to 53B to 53C; midvein, close to 70A. When opening and fully opened, lower surface: Close to 53B to 53C; midvein, close to 70A. Lateral petals: Length: About 1.2 cm to 1.4 cm. Width: About 0.9 cm to 1.1 cm. Shape: Spatulate. Apex: Emarginate. Base: Attenuate. Margin: Entire; undulate. Texture, upper and lower surfaces: Hirsute; rugose. Color: When opening and fully opened, upper surface: Close to 53B to 53C; midvein, close to 70A to 70B. When opening and fully opened, lower surface: Close to 53B to 53C; midvein, close to 70A to 70B. Lower petals: Length: About 0.9 cm to 1 cm. Width: About 4 mm to 6 mm. Shape: Spatulate. Apex: Emarginate. Base: Obtuse. Margin: Entire; undulate. Texture, upper and lower surfaces: Hirsute; rugose. Color: When opening and fully opened, upper surface: Close to 53B to 53C; midvein, close to 70A to 70B. When opening and fully opened, lower surface: Close to 53B to 53C; midvein, close to 70A to 70B.

*Calyx.*—Arrangement/shape: Six sepals fused in a single whorl; calyx, cylindrical tube-shaped. Length: About 1.4 cm to 1.6 cm. Width: About 1.1 cm to 1.2 cm. Texture, upper (inner) and lower (outer) surfaces: Smooth, glabrous; Intervenal areas, membraneous. Color, upper (inner) surface: Below stamen attachment, close to 145C to 145D; veins, close to 144C; above stamen attachment, 145B to 145D; veins, between 70A and 72A. Color, lower (outer)

surface: Close to 145C; veins, close to 144A or flushed with between N77A and 200B; large patches at petal attachment, close to 144B.

*Pedicels.*—Length: About 2 mm. Diameter: About 1 mm. Strength: Strong. Texture: Hirsute. Color: Between 142A to 142B.

*Reproductive organs.*—Stamens: Quantity per flower: About eleven; lower half of stamen adnate to the calyx. Filament length: About 3 mm to 4 mm. Filament color: Nine filaments, close to 150D; two filaments, close to 61C. Anther color: Nine anthers, close to 150D; two anthers, close to 91A. Pollen amount: Sparse. Pollen color: Close to 156C. Pistils: Quantity: One per flower. Pistil length: About 1.8 cm to 2 cm. Style length: About 1.3 cm to 1.4 cm. Style color: Close to 145C; towards the stigma, close to 56C. Stigma color: Between 64C and 64D. Ovary length: About 5 mm to 6 mm. Ovary color: Close to 145C. Fruits/seeds: Fruit and seed production have not been observed on plants of the new *Cuphea*.

Garden performance: Plants of the new *Cuphea* have been observed to have good garden performance and tolerate wind, rain and a wide range of temperatures.

Pathogen/pest resistance: Plants of the new *Cuphea* have not been observed to be resistant to pathogens and pests common to *Cuphea*.

It is claimed:

1. A new and distinct *Cuphea* plant named 'Ri Reeda' as illustrated and described.

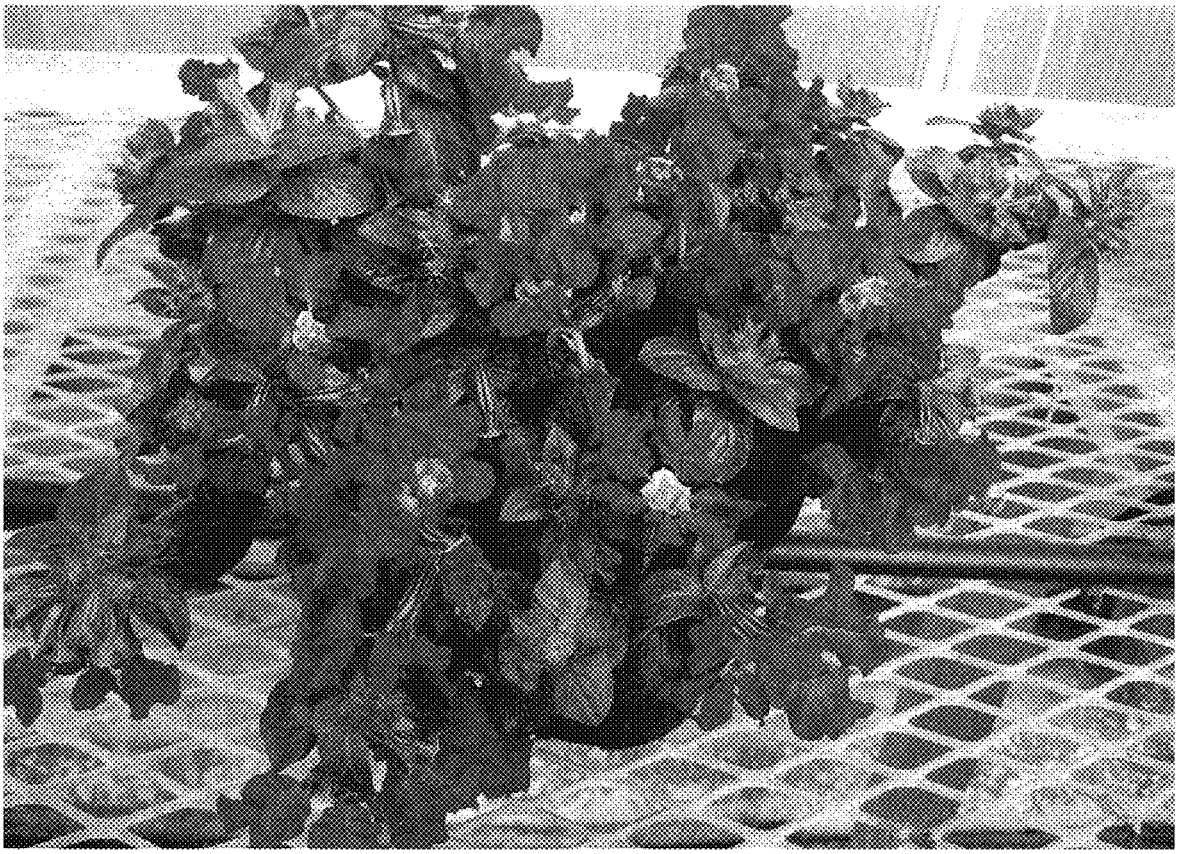

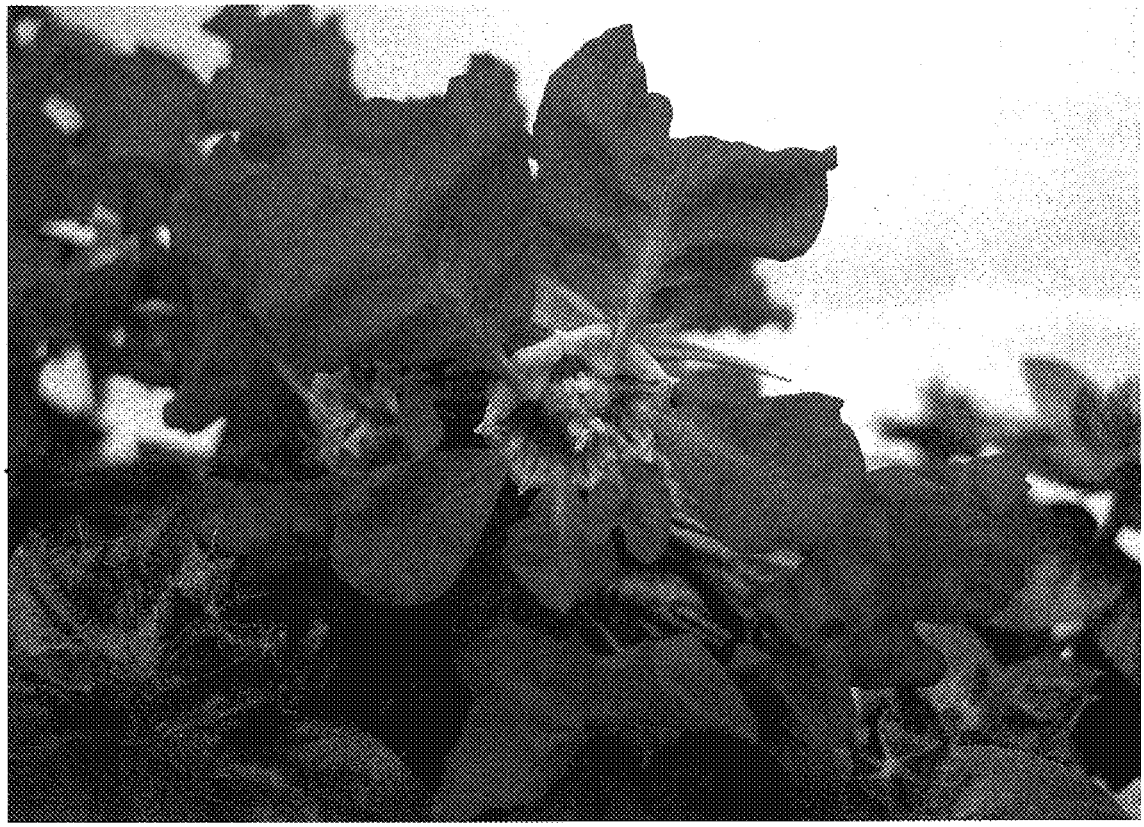

* * * * *